US012594005B2

(12) United States Patent
Hsu et al.

(10) Patent No.: US 12,594,005 B2
(45) Date of Patent: Apr. 7, 2026

(54) GRASPING-RESPONSE EVALUATION SYSTEM

(71) Applicant: National Cheng Kung University, Tainan City (TW)

(72) Inventors: Hsiu-Yun Hsu, Tainan City (TW); Li-Chieh Kuo, Tainan City (TW); Fong-Chin Su, Tainan City (TW); Kang-Chin Yang, Pingtung County (TW)

(73) Assignee: National Cheng Kung University, Tainan City (TW)

( * ) Notice: Subject to any disclaimer, the term of this patent is extended or adjusted under 35 U.S.C. 154(b) by 783 days.

(21) Appl. No.: 18/066,438

(22) Filed: Dec. 15, 2022

(65) Prior Publication Data

US 2023/0404438 A1 Dec. 21, 2023

(30) Foreign Application Priority Data

Jun. 21, 2022 (TW) .................................. 111123060

(51) Int. Cl.
 *A61B 5/11* (2006.01)
 *A61B 90/00* (2016.01)
(52) U.S. Cl.
 CPC ....... *A61B 5/1125* (2013.01); *A61B 2090/061* (2016.02); *A61B 2090/064* (2016.02); *A61B 2090/067* (2016.02)
(58) Field of Classification Search
 CPC ....... A61B 5/1125; A61B 5/224; A61B 5/225; A61B 5/4082; A61B 2090/064; A61B 2090/065; A61H 1/0285; A61H 1/0288; A61H 2201/1635
 See application file for complete search history.

(56) References Cited

U.S. PATENT DOCUMENTS

2006/0293615 A1* 12/2006 Valero-Cuevas ...... A61B 90/06
600/595

FOREIGN PATENT DOCUMENTS

CN 110123346 A * 8/2019 ............. G16H 20/30

OTHER PUBLICATIONS

Translation of CN 110123346 (Year: 2019).*

* cited by examiner

*Primary Examiner* — Devin B Henson
(74) *Attorney, Agent, or Firm* — MUNCY, GEISSLER, OLDS & LOWE, P.C.

(57) ABSTRACT

A grasping-response evaluation system includes: a base mechanism; a positioning module mounted in the base mechanism; a controlling device operable to control the positioning module to switch between the grasping and releasing states; a bob to be engaged with the positioning module in the grasping state; and a traction rope connected between the bob and the base mechanism. When the positioning module switches from the grasping state to the releasing state, the bob becomes disengaged from the positioning module, falls downwardly relative to the base mechanism, and simultaneously pulls down the traction rope. When a grasping-data collecting device removably disposed on the base mechanism and connected to the traction rope is lifted by a user's hand, it pulls up the traction rope, and measures a grasping force of the user's hand.

13 Claims, 7 Drawing Sheets

GRASPING-RESPONSE EVALUATION SYSTEM

CROSS-REFERENCE TO RELATED APPLICATION

This application claims priority to Taiwanese Invention Patent Application No. 111123060, filed on Jun. 21, 2022.

FIELD

The disclosure relates to an evaluation system, and more particularly to a grasping-response evaluation system.

BACKGROUND

In clinical assessment and diagnosis, when assessing the impact of neural damage to hand function, the grasping response (i.e., the grasp reflex, which is an involuntary flexion-adduction movement involving the hands and digits) of a patient's hand is generally regarded as an important indicator of neural development for occupational therapists to make clinical decisions. Specifically, with regard to the grasping response in daily situations, a functioning hand should be able to promptly and effectively adjust its grip force, according to somatosensory feedback induced by unexpected interferences, to maintain grip stability. Therefore, analysis of the grasping response in environments with interferences is of great significance in evaluating the hand function.

However, a conventional method for evaluating hand function that provides the patient with a gripping device to grasp can only conduct evaluation by measuring the grip force of the patient's hand without taking into account the effect of interferences. Although some research institutes have developed a method of using an exoskeleton to position the patient's limbs so as to measure the response of the patient's hand or limbs under interferences, movement of the patient's hand is often restricted by the exoskeleton such that the patient's reaction cannot be naturally expressed, or fully measured by such method.

SUMMARY

Therefore, an object of the disclosure is to provide a grasping-response evaluation system that can alleviate at least one of the drawbacks of the prior art.

According to the disclosure, the grasping-response evaluation system is adapted to evaluate a grasping response of a user's hand. The grasping-response evaluation system includes a base mechanism, a falling interference device, a controlling device and a grasping-data collecting device. The falling interference device includes a positioning module that is mounted in the base mechanism and that is controllable to switch between a grasping state and a releasing state, a bob that is configured to be engaged with the positioning module when the positioning module is in the grasping state, and a traction rope that has one end connected to the bob and the other end extending upwardly through a top end of the base mechanism for placing the bob in a suspended position. When the positioning module switches from the grasping state to the releasing state, the bob becomes disengaged from the positioning module, falls downwardly relative to the base mechanism, and simultaneously pulls down the traction rope. The controlling device is signally connected to the positioning module, and is operable to control the positioning module to switch between the grasping state and the releasing state. The grasping-data collecting device is removably disposed on the base mechanism, is connected to the other end of the traction rope, is configured to pull up on the traction rope when being moved up by the user's hand, and is configured to measure a grasping force of the user's hand.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
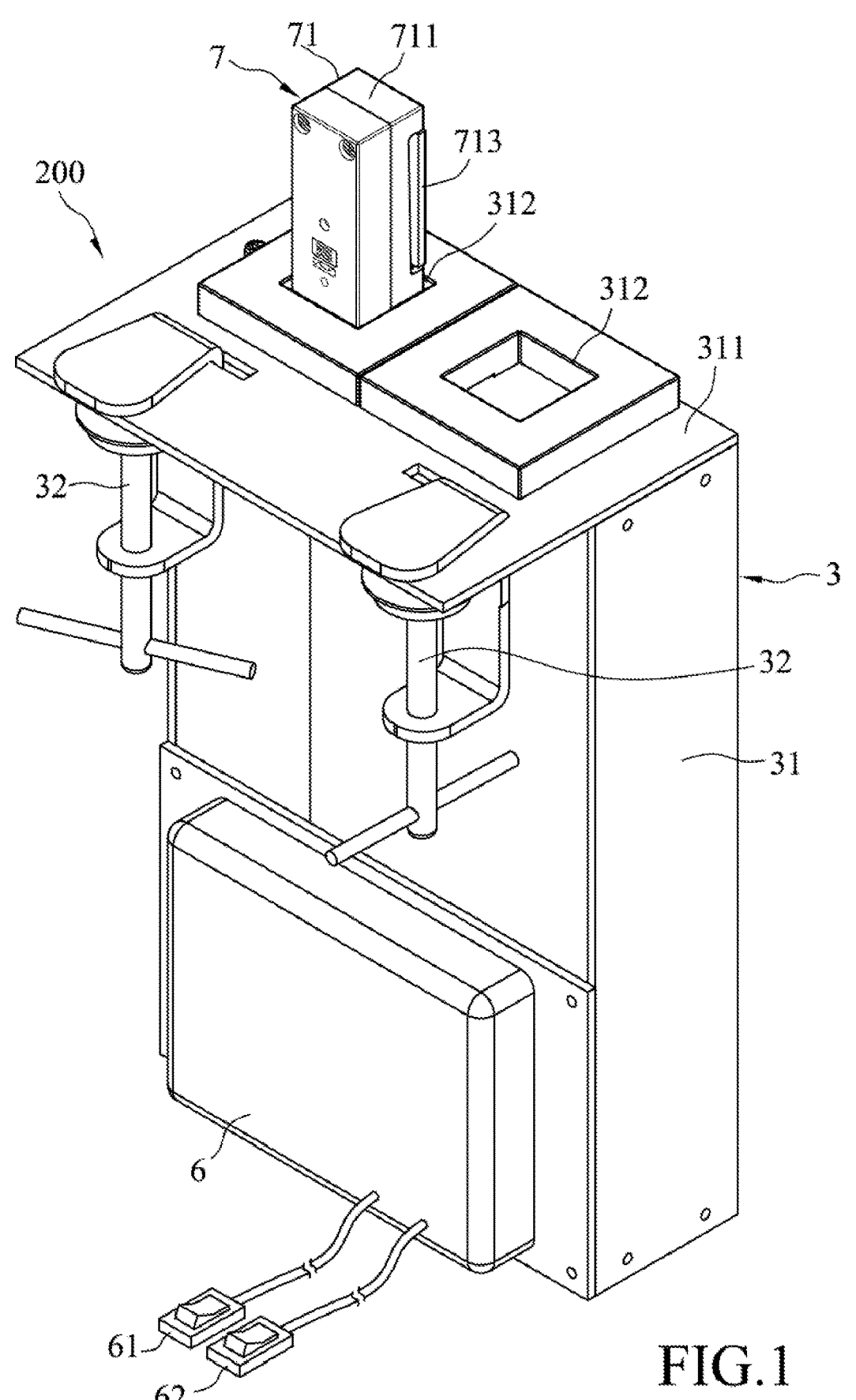
FIG. 1 is a perspective view of an embodiment of a grasping-response evaluation system according to the disclosure.

Before the disclosure is described in greater detail, it should be noted herein that for clarity of description, spatially relative terms such as "top," "bottom," "upper," "lower," "on," "above," "over," "downwardly," "upwardly" and the like may be used throughout the disclosure while making reference to the features as illustrated in the drawings. The features may be oriented differently (e.g., rotated 90 degrees or at other orientations) and the spatially relative terms used herein may be interpreted accordingly.

Figure 2:
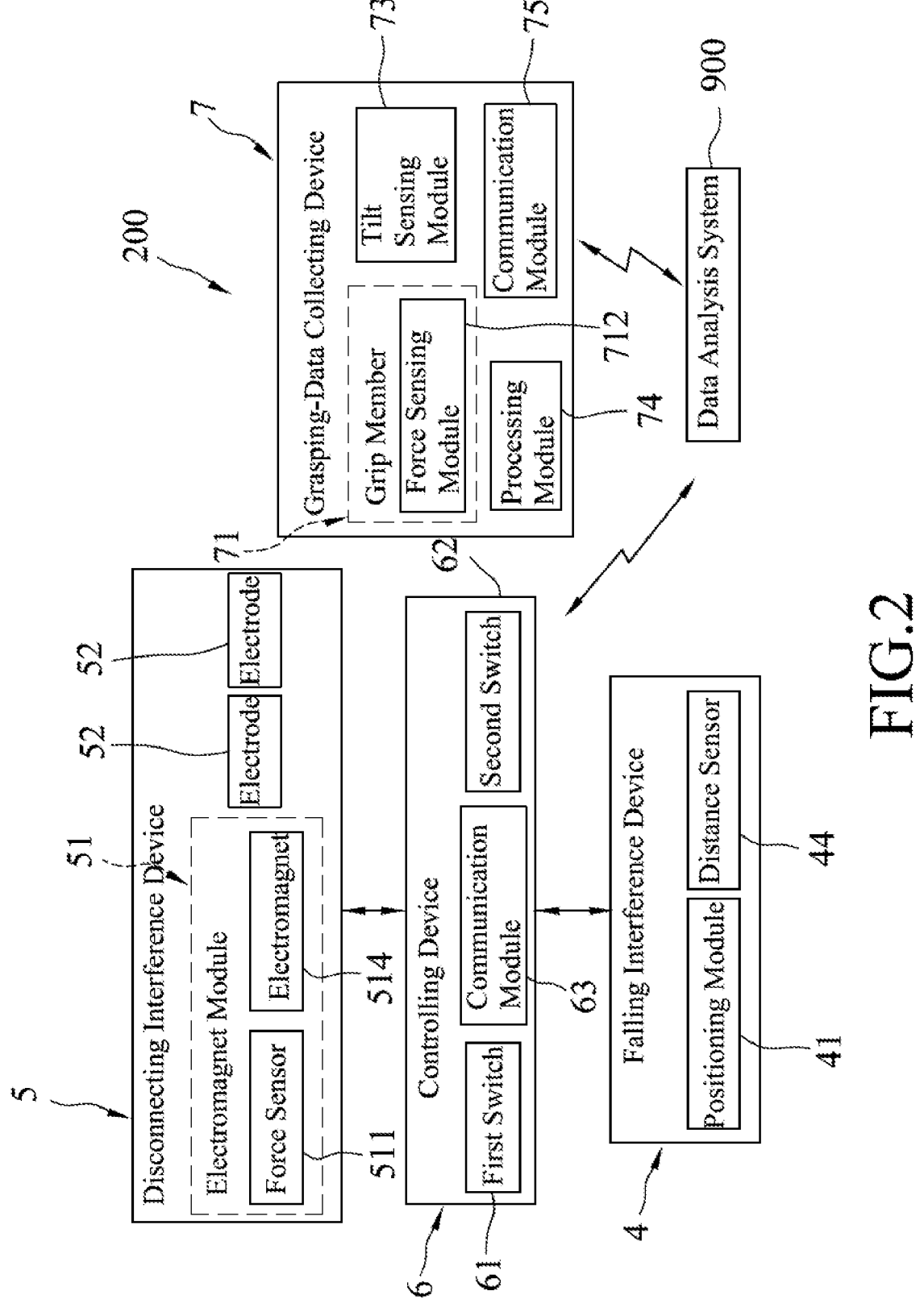
FIG. 2 is a block diagram illustrating the functional architecture of the embodiment.

Referring to FIGS. 1 and 2, an embodiment of a grasping-response evaluation system 200 according to the disclosure is adapted to evaluate a grasping response of a user's hand in environments with interferences, and to transmit signals to a data analysis system 900 for evaluating sensorimotor control state of the user's hand.

The grasping-response evaluation system 200 includes a base mechanism 3, a falling interference device 4 mounted to the base mechanism 3, a disconnecting interference device 5, a controlling device 6, and a grasping-data collecting device 7 disposed on the base mechanism 3 and adapted for the user's hand to grasp.

Figure 3:
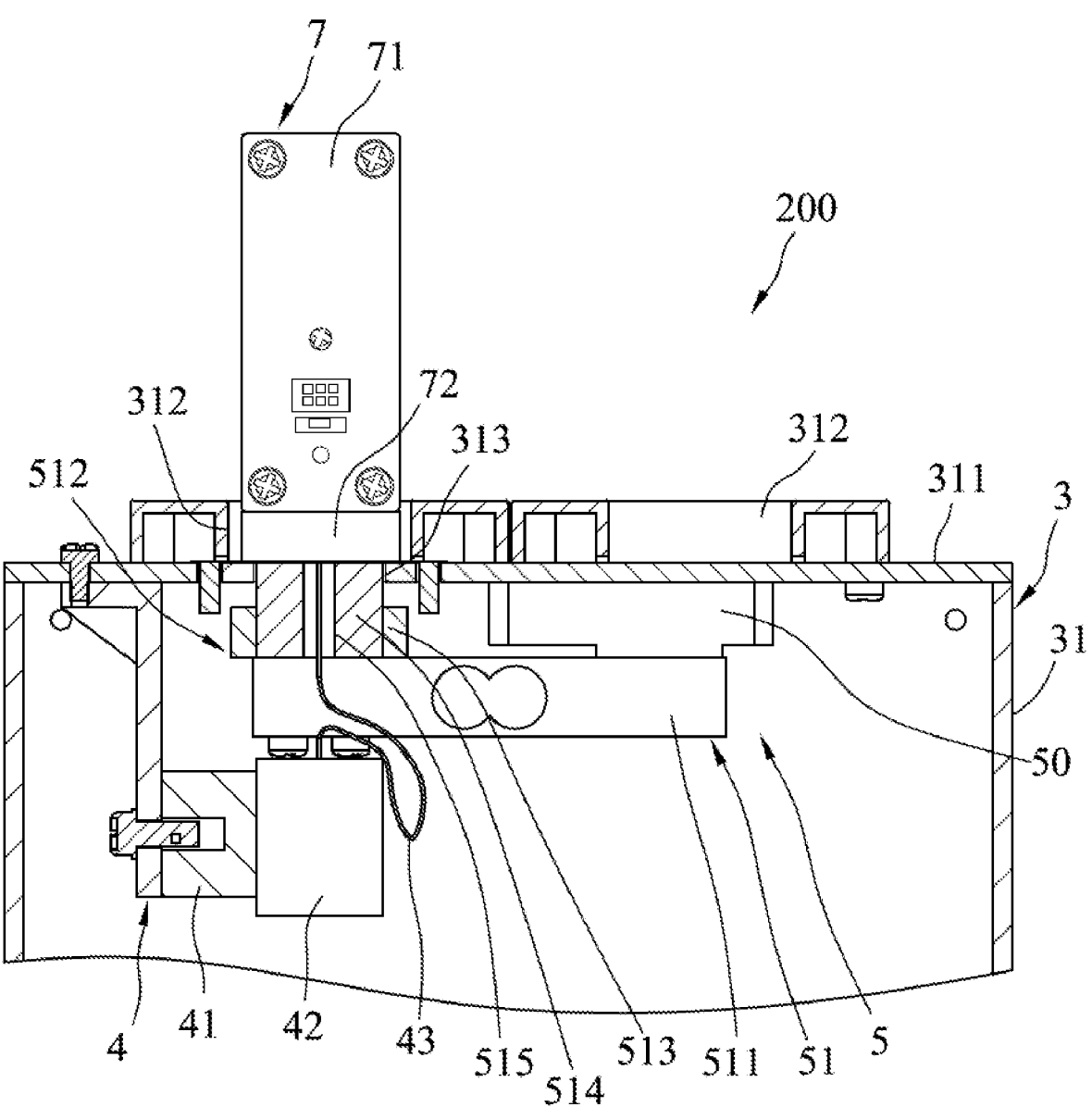
FIG. 3 is a fragmentary sectional view of the embodiment, illustrating a bob being engaged with a positioning module, and a grasping-data collecting device being disposed at a testing position.
Figure 4:
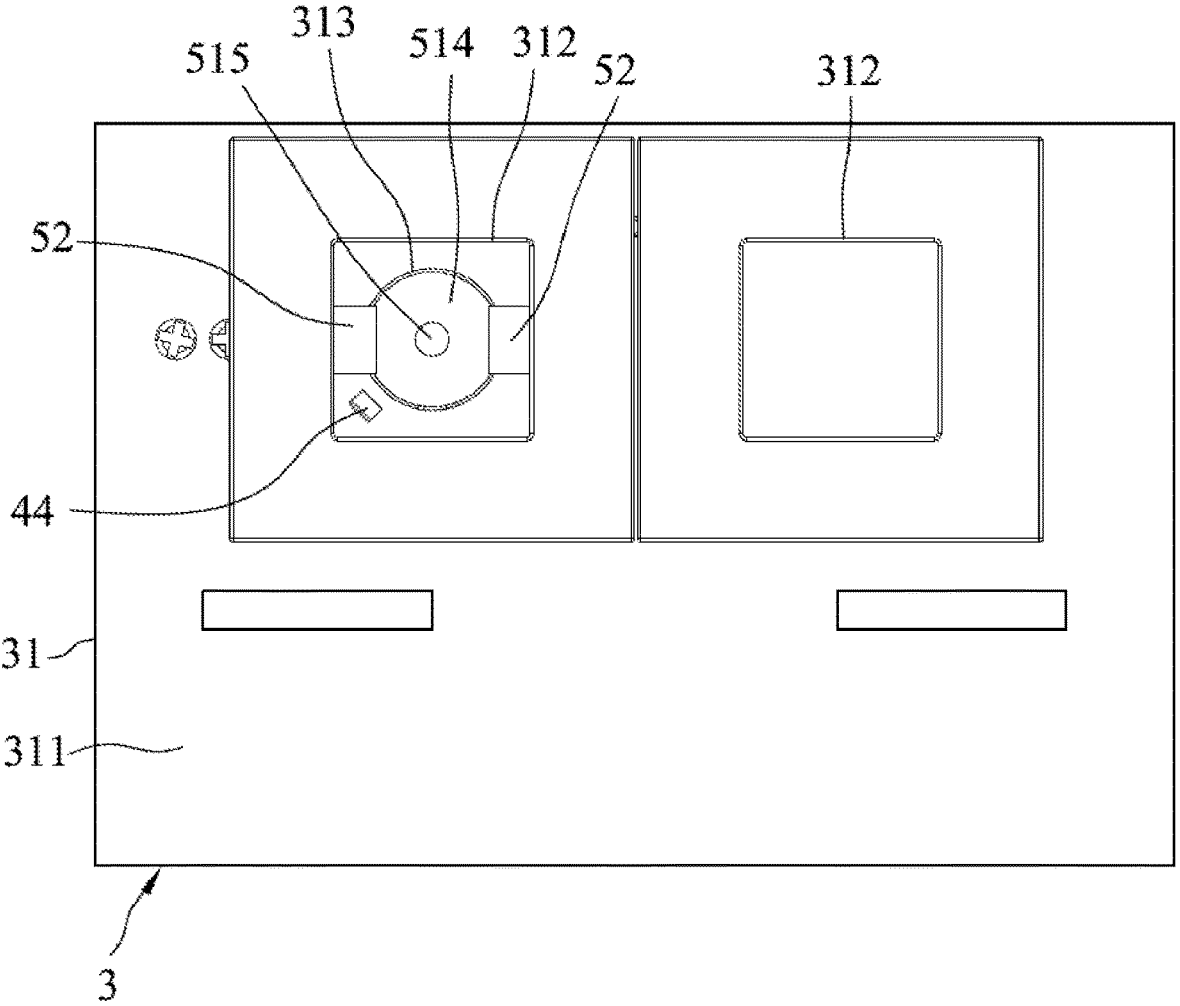
FIG. 4 is a top plan view of the embodiment.

Referring to FIGS. 1, 3, and 4, the base mechanism 3 includes a hollow base seat 31 that extends along an up-down direction, and two frame units 32 that are mounted to the base seat 31 and that are spaced part from each other along a left-right direction. The base seat 31 has a top wall 311 that has a top surface formed with a plurality of spaced-apart hollow seats 312, and that is formed with a through slot 313 extending along the up-down direction and spatially communicating an adjacent one of the hollow seats 312. Each of the hollow seats 312 opens upwardly, and is provided for the grasping-data collecting device 7 to be removably inserted thereinto.

Each of the frame units 32 is adapted to clamp a table board (not shown) therebetween, so as to hang the base seat 31 on a side of the table board. It should be noted that, configuration of the frame units 32 for positioning the base seat 31 is not limited to the present embodiment as illustrated in the drawings, and may vary greatly among embodiments. However, since the configuration of the frame units 32 is not the focus of the disclosure, it will not be described further hereinafter.

Figure 5:
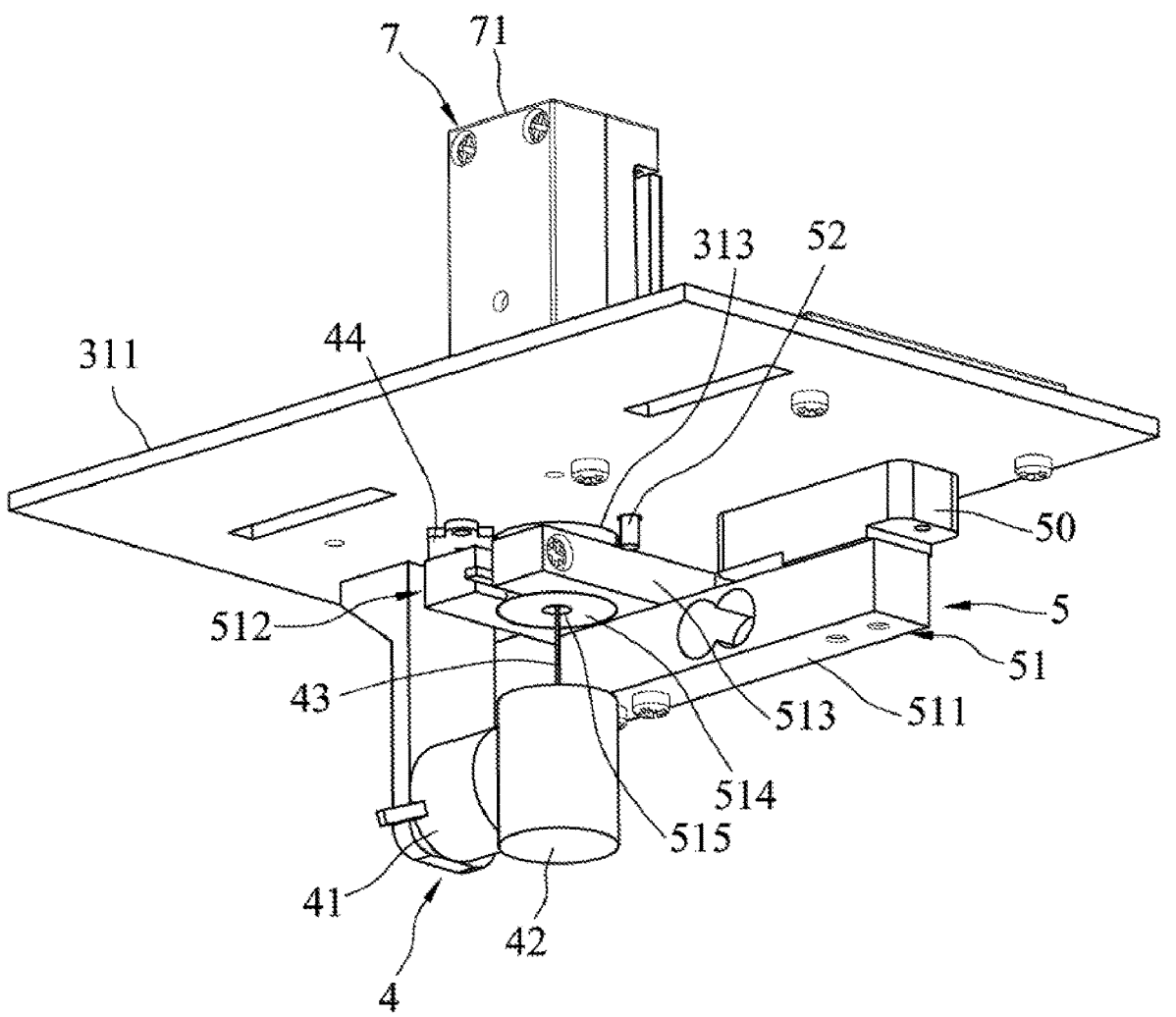
FIG. 5 is a perspective view illustrating a falling interference device and a disconnecting interference device of the embodiment.

Referring to FIGS. 3, 4, and 5, the falling interference device 4 includes a positioning module 41, a bob 42, a traction rope 43 and a distance sensor 44. The positioning module 41 is mounted in the base seat 31 of the base mechanism 3, and is disposed below and spaced apart from the top wall 311 of the base seat 31. The bob 42 is disposed below the top wall 311 of the base seat 31, is movable along the up-down direction relative to the base seat 31, and is configured to be engaged with the positioning module 41. The traction rope 43 has one end connected to the bob 42 and the other end extending upwardly through the through slot 313 of the top wall 311 and the hollow seat 312 (i.e., the hollow seat 312 adjacent to the through slot 313) to be connected to the grasping-data collecting device 7 for placing the bob 42 in a suspended position. The distance sensor 44 is mounted to the top wall 311 of the base seat 31, and is exposed from the top surface of the top wall 311 at a bottom of the adjacent hollow seat 312.

The positioning module 41 is signally connected to the controlling device 6, and is controllable by the controlling device 6 to switch between a grasping state and a releasing state. When the positioning module 41 is in the grasping state, the bob 42 is engaged with and positioned by the positioning module 41. When the positioning module 41 switches from the grasping state to the releasing state, the bob 42 becomes disengaged from the positioning module 41, falls downwardly relative to the base mechanism 3, and simultaneously pulls down the traction rope 43.

Specifically, in the present embodiment, the positioning module 41 is an electromagnet, and the bob 42 is a ferromagnetic metal. When in the grasping state, the positioning module 41 is configured to be magnetized so as to attract and secure the bob 42 in position; when in the releasing state, the positioning module 41 is configured to be demagnetized so as to release the bob 42. However, it should be noted that configuration of the positioning module 41 is not limited to the present embodiment. In other embodiments of the disclosure, the positioning module 41 may, for example, be configured to position the bob 42 by clamping the bob 42 therebetween, or by extending into the bob 42 in a detachably engaging manner.

The distance sensor 44 is signally connected to the controlling device 6, and is configured for measuring an object's moving distance along an opening direction (i.e., an upward direction) of the adjacent hollow seat 312. Specifically, in the present embodiment, when the grasping-data collecting device 7 inserted in the adjacent hollow seat 312 is moved upwardly, the distance sensor 44 is configured to measure an upward moving distance of the grasping-data collecting device 7 from the base mechanism 3, to generate a distance signal therefrom, and to transmit the distance signal to the controlling device 6. In the present embodiment, the distance sensor 44 is an optical distance sensor. However, in other embodiments of the disclosure, the distance sensor 44 may be configured as other types of distance sensors, such as ultrasonic distance sensors, and not limited to the present configuration.

The disconnecting interference device 5 is mounted in the base mechanism 3, and includes an electromagnet module 51 that is disposed in the base seat 31 of the base mechanism 3 below the top wall 311, and two electrodes 52 that are mounted to the top wall 311, that are disposed around the through slot 313 of the top wall 311, and that are exposed at the bottom of the adjacent hollow seat 312. The electromagnet module 51 includes a force sensor 511 that is signally connected to the controlling device 6, and that is mounted below the top wall 311, and an electromagnet unit 512 that is signally connected to the controlling device 6, and that is disposed on the force sensor 511 and directly below the through slot 313 of the top wall 311. Specifically, the force sensor 511 has an elongated bar shape, and has one end segment connected to the top wall 311 via a connecting seat 50, and an opposite end segment suspended below the top wall 311, and provided for the electromagnet unit 512 to be disposed thereon. The force sensor 511 is configured to measure an upward force of the electromagnet unit 512 along the up-down direction, to generate a force signal therefrom, and to transmit the force signal to the controlling device 6. In the present embodiment, the force sensor 511 is a strain gauge or a load cell. However, the force sensor 511 is not limited to the aforementioned, and may be, for example, a pressure sensor in other embodiments of the disclosure.

The electromagnet unit 512 of the electromagnet module 51 includes a mounting seat 513 that is fixed to the end segment of the force sensor 511 that is suspended below the top wall 311, and an electromagnet 514 that is fixedly mounted to the mounting seat 513, that is received in the through slot 313 of the top wall 311, and that is movable relative to the through slot 313 along the up-down direction. The electromagnet 514 is controllable by the controlling device 6 to switch between a magnetized state that generates a magnetic field, and a demagnetized state that removes the magnetic field, and is formed with a through hole 515 that extends along the up-down direction, and that spatially communicates with the through slot 313. The traction rope 43 extends movably through both the through hole 515 and the through slot 313.

The electrodes 52 are signally connected to the controlling device 6, and are configured to be connected to and electrified by the grasping-data collecting device 7 that is inserted in the adjacent hollow seat 312, thereby triggering the controlling device 6 to control the electromagnet 514 of the electromagnet module 51 to switch to the magnetized state.

The controlling device 6 is signally connected to the falling interference device 4 and the disconnecting interference device 5, and includes a communication module 63 that is adapted for signal communication and data transmission with the data analysis system 900, and a first switch 61 and a second switch 62 that are adapted for manually operation.

Referring to FIGS. 1, 2, and 3, upon receipt of the distance signal from the distance sensor 44, the controlling device 6 is configured to control the positioning module 41 to switch from the grasping state to the releasing state when the corresponding upward moving distance of the grasping-data collecting device 7 is greater than or equal to a distance threshold value. Similarly, upon receipt of the force signal from the force sensor 511, the controlling device 6 is configured to control the electromagnet 514 of the electromagnet module 51 to switch from the magnetized state to the demagnetized state when the corresponding upward force is greater than or equal to a force threshold value. Further, the first switch 61 of the controlling device 6 is operable to control the positioning module 41 to switch between the grasping state and the releasing state, and the second switch 62 of the controlling device 6 is operable to control the electromagnet module 51 to switch between the magnetized state and the demagnetized state. The controlling device 6 further generates interference test data based on the upward movement distance measured by the distance sensor 44, the upward force measured by the force sensor 511, and information of state changes and change times of the positioning module 41 and the electromagnet 514, and is adapted to transmit the interference test data to the data analysis system 900 via the communication module 63.

Figure 6:
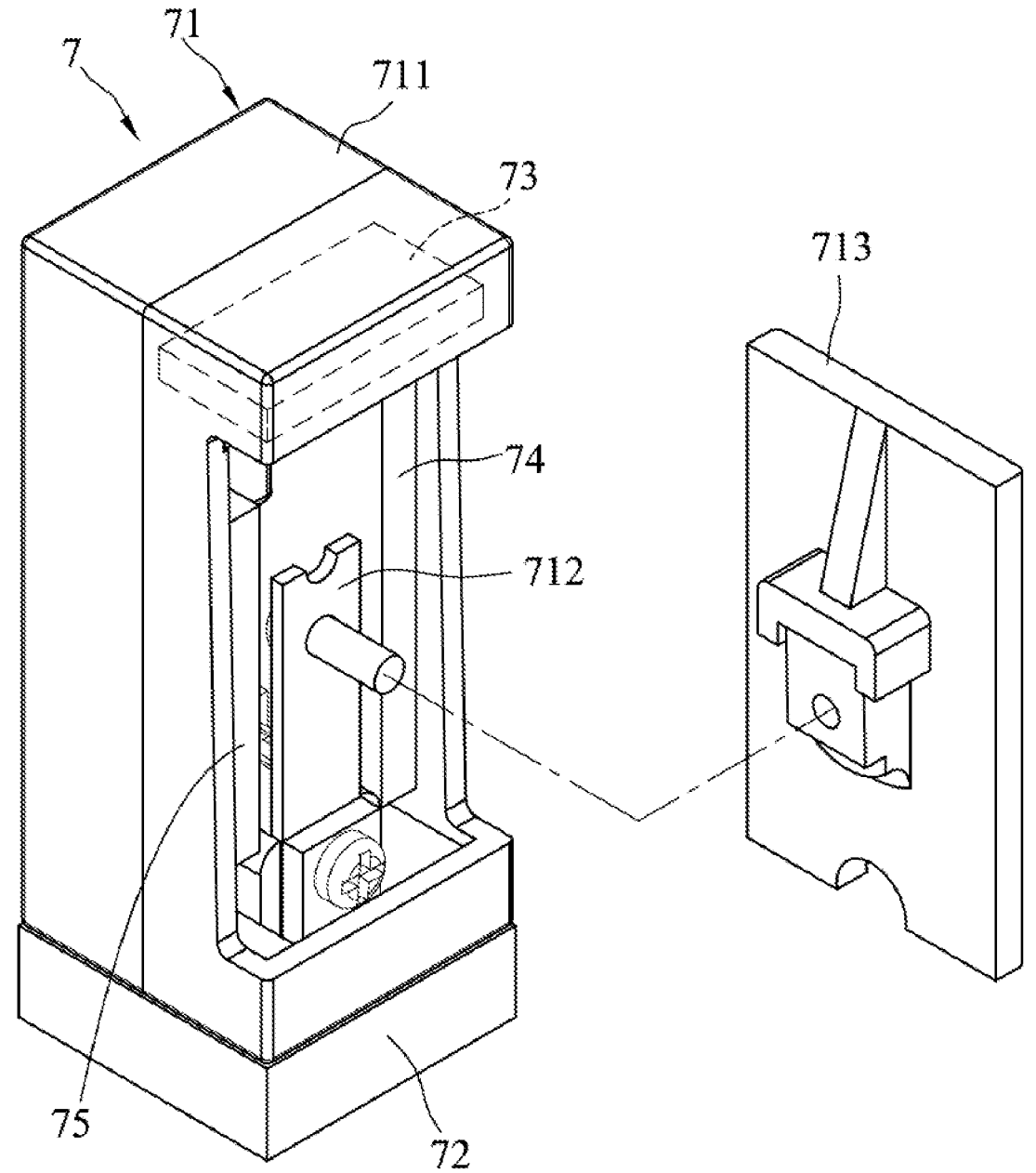
FIG. 6 is a partially exploded perspective view of the grasping-data collecting device of the embodiment.

Referring to FIGS. 2, 4, and 6, the grasping-data collecting device 7 includes a grip member 71 that is adapted for the user's hand to grasp, a metallic member 72 that is disposed at a bottom end of the grip member 71, and a tilt sensing module 73, a processing module 74 and a communication module 75 that are mounted in the grip member 71. The grasping-data collecting device 7 is manually movable relative to the base seat 31 between a testing position, where the grasping-data collecting device 7 is received in and positioned by the adjacent hollow seat 312 of the base seat 31 and where the metallic member 72 is attracted by the electromagnet 514 of the electromagnet module 51 in the magnetized state, an idling position, where the grasping-data collecting device 7 is received in the other one of the hollow seat 312 (i.e., the one not in spatial communication with the through slot 313) and where the metallic member 72 is prevented from being attracted by the electromagnet 514 of the electromagnet module 51, and a lifted position, where the grasping-data collecting device 7 is not received in any one of the hollow seats 312 and is spaced apart from the base mechanism 3.

The grip member 71 is configured to measure a grasping force of the user's hand during a grasping period to obtain force data. In the present embodiment, the grip member 71 has a casing 711 that extends along the up-down direction, a force sensing module 712 that is disposed in the casing 711, and an operation panel 713 that is mounted to the force sensing module 712 and that is embedded to one side of the casing 711. The casing 711 and the operation panel 713 are adapted to be grasped and moved by the user's hand during operation, so as to trigger the force sensing module 712 to measure the force data. In the present embodiment, the force sensing module 712 includes a strain gauge or a load cell. However, the force sensing module 712 is not limited to the aforementioned, and may include, for example, a pressure sensor in other embodiments of the disclosure. In addition, the configuration of the grip member 71 is not limited to that illustrated in the drawings of the disclosure, and may vary in other embodiments of the disclosure.

Since the metallic member 72 is disposed at the bottom end of the grip member 71, when the grasping-data collecting device 7 is inserted into the adjacent hollow seat 312 (i.e., the grasping-data collecting device 7 is at the testing position), the metallic member 72 is brought into contact with and electrifies the electrodes 52, thereby triggering the controlling device 6 to control the electromagnet 514 of the electromagnet module 51 to switch to the magnetized state. As a result, the metallic member 72 becomes magnetically attracted and positioned by the electromagnet 514 of the electromagnet module 51 in the magnetized state.

The tilt sensing module 73 is disposed in the grip member 71, and is configured to measure a tilt angle of the grip member 71 and accelerations of the grip member 71 in three axial directions during the grasping period to obtain angle data and acceleration data. It should be noted that, the tilt sensing module 73 is a three-axis sensor in the present embodiment, but is not limited thereto in other embodiments of the disclosure.

The processing module 74 is disposed in the grip member 71, is signally connected to the grip member 71 and the tilt sensing module 73, and is configured to generate grasping data based on the force data, the angle data, and the acceleration data of the grasping period. The communication module 75 is configured to transmit the grasping data to the data analysis system 900.

It should be noted that, the communication module 63, 75 are configured to communicate signals with and transmit data to the data analysis system 900 through various wired (e.g., traditional cable products) or wireless communication technologies (e.g., Bluetooth, Wi-Fi, 4G, and 5G).

Referring to FIGS. 1, 3, and 4, the following describes a testing operation of the present embodiment of the grasping-response evaluation system 200, during which the grasping responses of two testing stages, i.e., an upward-pulling-force interference stage and a downward-pulling-force interference stage, are evaluated successively.

Prior to the testing operation, the grasping-data collecting device 7 is inserted into the hollow seat 312 adjacent to the through slot 313, such that the metallic member 72 is connected to and electrifies the electrodes 52, thereby triggering the controlling device 6 to control the electromagnet 514 to switch to the magnetized state, and to magnetically attract and position the grasping-data collecting device 7 in the testing position. In addition, the positioning module 41 is controlled by the controlling device 6 to switch to the grasping state, and the bob 42 is engaged with and positioned by the positioning module 41.

Figure 7:
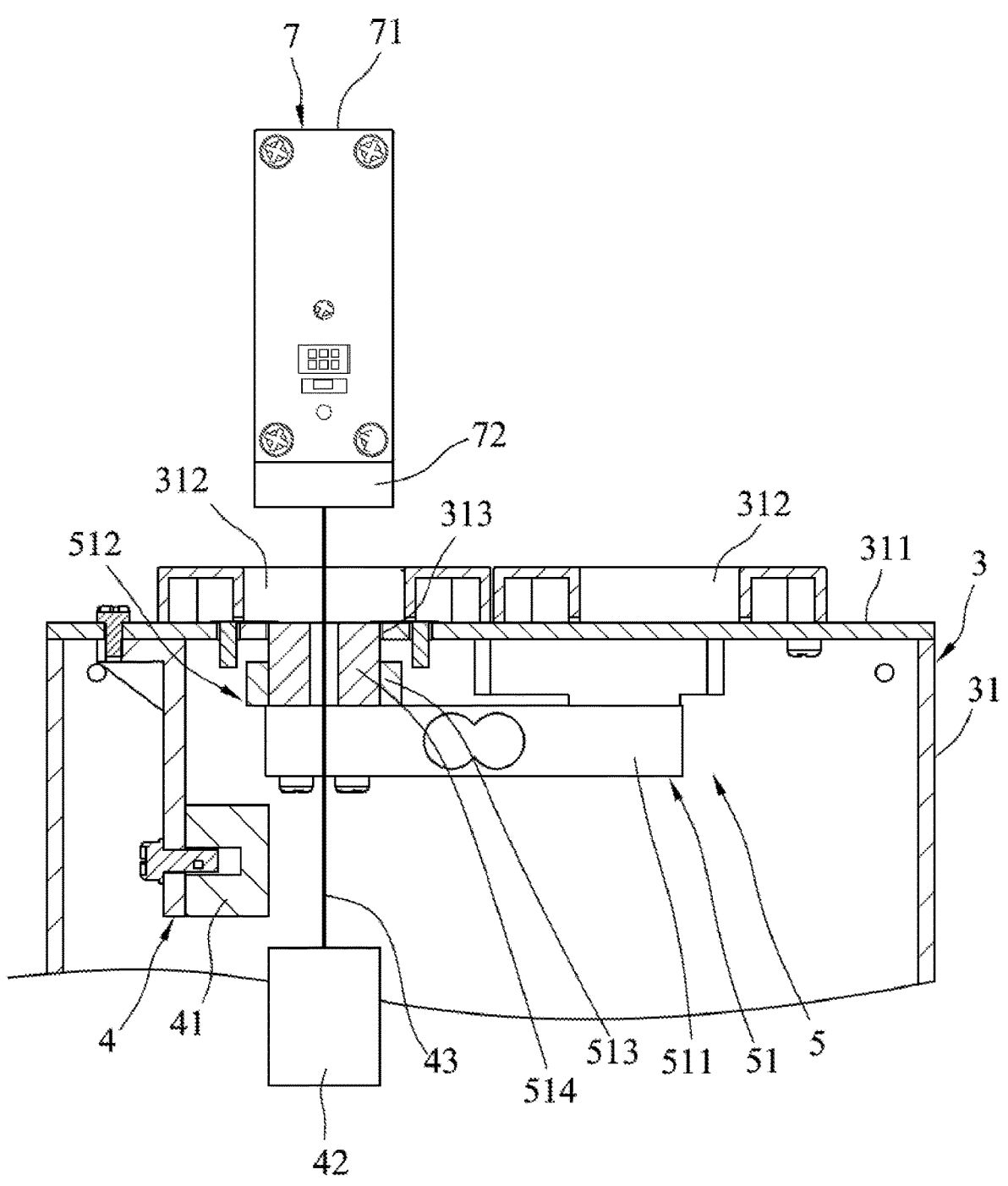
FIG. 7 is a view similar to FIG. 3, but illustrating the bob being released by the positioning module, and the grasping-data collecting device being disposed at a lifted position.

Referring to FIGS. 2, 3, and 7, when the testing operation starts and enters the upward-pulling-force interference stage, the user is requested to start grasping and pulling the grip member 71 up from the base seat 31. During this time, the grip member 71 pulls the electromagnet 514 upwardly via the metallic member 72, thus moving and deforming the force sensor 511 and generating the force signal. Upon receipt of the force signal, the controlling device 6 determines whether the corresponding upward force is greater than or equal to the force threshold value, and if in the affirmative, the controlling device 6 controls the electromagnet 514 to switch from the magnetized state to the demagnetized state to release the metallic member 72, so that the grasping-data collecting device 7 is allowed to be pulled up from the base seat 31 (i.e., the user will notice a sudden elimination of a downward pulling force). At this point, the upward-pulling-force interference stage is completed.

When the grasping-data collecting device 7 is pulled away from the base seat 31, the testing operation enters the downward-pulling-force interference stage. During this stage, the distance sensor 44 measures the upward moving distance of the metallic member 72 and generates the distance signal. Upon receipt of the distance signal, the controlling device 6 determines whether the corresponding upward moving distance is greater than or equal to the distance threshold value, and if in the affirmative, the controlling device 6 controls the positioning module 41 to switch from the grasping state to the releasing state to release the bob 42, so that the bob 42 begins to fall and simultaneously pulls down the traction rope 43. At the instant the traction rope 43 is stretched by the bob 42, a downward impact force is exerted on the grasping-data collecting device 7. If, at this instant, the user does not respond immediately to adjust the grip force, the grasping-data collecting device 7 may be pulled out of the grip of the user's hand.

In addition, when the grasping-data collecting device 7 is removed from the adjacent hollow seat 312, the user may be requested to insert the grasping-data collecting device 7 into the other hollow seat 312 at the idling position.

It should be noted that, during the above-mentioned upward-pulling-force interference stage and downward-pulling-force interference stage, the grip member 71 continuously measures the grasping force to generate the force data, and the tilt sensing module 73 continuously measures the tilt angle and the accelerations to generate the angle data and acceleration data, so that processing module 74 is able to generate the grasping data based on all the force and angle data and then transmit the grasping data to the data analysis system 900 through the communication module 75.

It should also be noted that, during the above-mentioned two interference stages, a test evaluator may control the positioning module 41 to switch to the releasing state, and the electromagnet 514 the demagnetized state, by manually operating the first and second switches 61, 62 of the controlling device 6, so as to exert unexpected interference on the operation to test the user's response. In addition, the upward-pulling-force interference stage and downward-pulling-force interference stage are not necessary to be performed successively in the same operation, and may be performed solely and independently.

In summary, by virtue of the falling interference device 4 and the disconnecting interference device 5, the present embodiment of the grasping-response evaluation system 200 is capable of a testing operation having two different interference stages. Further, by virtue of the configuration of the grasping-data collecting device 7, the grasping data of the user can be accurately obtained during the testing operation to better assist in clinical assessment and diagnosis of the sensorimotor control state of the user's hand.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s),
it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A grasping-response evaluation system adapted to evaluate a grasping response of a user's hand, comprising:
   a base mechanism;
   a falling interference device including a positioning module that is mounted in said base mechanism and that is controllable to switch between a grasping state and a releasing state, a bob that is configured to be engaged with said positioning module when said positioning module is in the grasping state, and a traction rope that has one end connected to said bob and the other end extending upwardly through a top end of said base mechanism for placing said bob in a suspended position, wherein, when said positioning module switches from the grasping state to the releasing state, said bob becomes disengaged from said positioning module, falls downwardly relative to said base mechanism, and simultaneously pulls down said traction rope;
   a controlling device signally connected to said positioning module, and being operable to control said positioning module to switch between the grasping state and the releasing state; and
   a grasping-data collecting device removably disposed on said base mechanism, connected to said other end of said traction rope, configured to pull up on said traction rope when being moved up by the user's hand, and configured to measure a grasping force of the user's hand.

2. The grasping-response evaluation system of claim 1, wherein said falling interference device further includes a distance sensor that is mounted in said base mechanism, and that is signally connected to said controlling device, said distance sensor being configured to measure an upward moving distance of said grasping-data collecting device from said base mechanism, to generate a distance signal therefrom, and to transmit said distance signal to said controlling device, said controlling device being configured to control said positioning module to switch from the grasping state to the releasing state upon receipt of said distance signal when the corresponding upward moving distance of said grasping-data collecting device is greater than or equal to a distance threshold value.

3. The grasping-response evaluation system of claim 2, further comprising a disconnecting interference device mounted in said base mechanism, and including an electromagnet module that is disposed in said base mechanism and that is signally connected to said controlling device, said electromagnet module being controllable by said controlling device to switch between a magnetized state that generates a magnetic field, and a demagnetized state that removes the magnetic field, said grasping-data collecting device including a grip member that is configured to measure the grasping force of the user's hand to obtain force data, and a metallic member that is disposed at a bottom end of said grip member, said grasping-data collecting device being manually movable between a testing position, where said grasping-data collecting device is disposed on a top end of said base mechanism and where said metallic member is attracted by said electromagnet module in the magnetized state, and a lifted position, where said grasping-data collecting device is spaced apart from said base mechanism.

4. The grasping-response evaluation system of claim 3, wherein said disconnecting interference device further includes two electrodes that are mounted to and exposed from said top end of said base mechanism, and that are signally connected to said controlling device, said electrodes being configured to be connected to and electrified by said metallic member when said grasping-data collecting device is at the testing position, thereby triggering said controlling device to control said electromagnet module to switch to the magnetized state.

5. The grasping-response evaluation system of claim 4, wherein said base mechanism has a top wall provided for said grasping-data collecting device to be disposed thereon at the testing position, said electrodes being exposed from said top wall, said electromagnet module including a force sensor that is mounted below said top wall, that is signally connected to said controlling device, and that is configured to measure an upward force, to generate a force signal therefrom, and to transmit said force signal to said controlling device, and an electromagnet unit that is disposed on said force sensor, that is signally connected to said controlling device, that is movable along an up-down direction relative to said top wall, and that is configured to magnetically attract said metallic member when said electromagnet module is in the magnetized state, said controlling device being configured to control said electromagnet module to switch from the magnetized state to the demagnetized state upon receipt of said force signal when the corresponding upward force is greater than or equal to a force threshold value.

6. The grasping-response evaluation system of claim 5, wherein said top wall is formed with a through slot that extends along the up-down direction, said electrodes being disposed around said through slot, said electromagnet unit of said electromagnet module including a mounting seat that is fixed to said force sensor, and an electromagnet that is mounted to said mounting seat, that is received in said through slot, and that is movable relative to said through slot along the up-down direction, said electromagnet being formed with a through hole that extends along the up-down direction, and that spatially communicates with said through slot, said traction rope extending movably through said through hole and said through slot.

7. The grasping-response evaluation system of claim 4, wherein said controlling device further includes a second switch that is operable to control said electromagnet module to switch between the magnetized state and the demagnetized state.

8. The grasping-response evaluation system of claim 3, wherein said grasping-data collecting device further includes a tilt sensing module that is disposed in said grip member, and that is configured to measure a tilt angle of said grip member and accelerations of said grip member in three axial directions to obtain angle data and acceleration data.

9. The grasping-response evaluation system of claim 8, wherein grasping-data collecting device further includes a processing module that is disposed in said grip member, and that is configured to generate grasping data based on said force data and said angle data, and a communication module that is configured to transmit said grasping data externally.

10. The grasping-response evaluation system of claim 3, wherein said base mechanism further has at least one hollow seat that opens upwardly, and that is configured to receive and position said grip member when said grasping-data collecting device is at the testing position.

11. The grasping-response evaluation system of claim 10, wherein said at least one hollow seat has a plurality of hollow seats, one of said hollow seats being configured to receive and position said grip member when said grasping-data collecting device is at the testing position, the other one of said hollow seats being configured to receive said grip member when said grasping-data collecting device is at an idling position, where said metallic member is prevented from being attracted by said electromagnet module.

12. The grasping-response evaluation system of claim 1, wherein said positioning module is an electromagnet, is configured to be magnetized in the grasping state so as to attract and secure said bob in position, and is configured to be demagnetized in the releasing state so as to release said bob.

13. The grasping-response evaluation system of claim 1, wherein said controlling device includes a first switch that is operable to control said positioning module to switch between the grasping state and the releasing state.

* * * * *